(12) United States Patent
Carinci et al.

(10) Patent No.: US 12,029,544 B2
(45) Date of Patent: Jul. 9, 2024

(54) METHOD FOR THE REDUCTION OF INTERFERENCE SIGNALS

(71) Applicant: Siemens Healthcare GmbH, Erlangen (DE)

(72) Inventors: Flavio Carinci, Würzburg (DE); Mario Zeller, Erlangen (DE); Dominik Paul, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 64 days.

(21) Appl. No.: 17/708,111

(22) Filed: Mar. 30, 2022

(65) Prior Publication Data
US 2022/0313104 A1    Oct. 6, 2022

(30) Foreign Application Priority Data
Mar. 31, 2021    (DE) ...................... 10 2021 203 268.0

(51) Int. Cl.
  *A61B 5/055*    (2006.01)
  *G01R 33/483*    (2006.01)
  *G01R 33/565*    (2006.01)

(52) U.S. Cl.
  CPC .......... *A61B 5/055* (2013.01); *G01R 33/4835* (2013.01); *G01R 33/56563* (2013.01)

(58) Field of Classification Search
  CPC ................ A61B 5/055; G01R 33/4835; G01R 33/56563
  See application file for complete search history.

(56) References Cited

U.S. PATENT DOCUMENTS

| 4,885,542 | A  | * | 12/1989 | Yao ................... | G01R 33/56518 |
|           |    |   |         |                        | 324/307 |
| 2014/0062479 | A1 | * | 3/2014 | Kannengiesser .. | G01R 33/4828 |
|           |    |   |         |                        | 324/309 |
| 2014/0266195 | A1 | * | 9/2014 | Levin ............... | G01R 33/56509 |
|           |    |   |         |                        | 324/309 |

(Continued)

OTHER PUBLICATIONS

Setsompop, K. et al. "Improving diffusion MRI using simultaneous multi-slice echo planar imaging" NeuroImage, vol. 63, pp. 569-580, 2012; (Internet: The slice-GRAPPA algorithm (Setsompop et al., 2012) was used to unalias the multiple slices.); 2012.

(Continued)

*Primary Examiner* — Dixomara Vargas
(74) *Attorney, Agent, or Firm* — Banner & Witcoff Ltd.

(57) ABSTRACT

The disclosure relates to techniques for acquiring measured data that has been recorded simultaneously via a magnetic resonance facility from at least two slices from an examination object comprising at least two different spin types. The techniques includes selecting a desired simultaneous recording of measured data from at least two slices in which during recording phases that generate field of view shifts have been imprinted, selecting a compensation factor to compensate for interference signals caused by the different spin types, determining a compensation phase for the phases to be imprinted in the desired recording as a function of the compensation factor, and carrying out the desired recording of measured data and/or reconstruction of image data from the measured data by applying the compensation phase that has been determined to the respective phases to be imprinted.

19 Claims, 2 Drawing Sheets

(56) References Cited

U.S. PATENT DOCUMENTS

Figure 1:
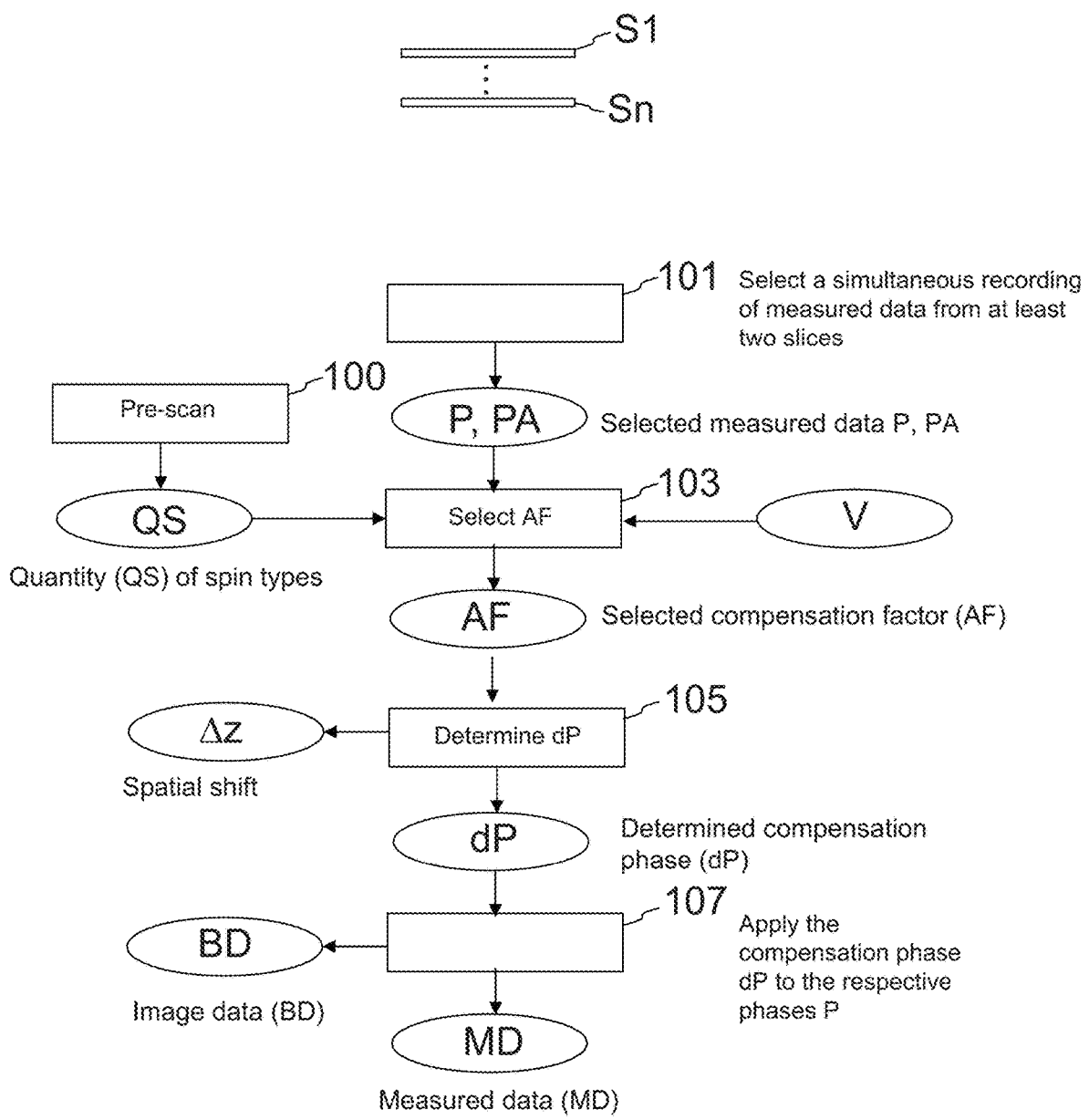

2018/0210059 A1 7/2018 Park et al.
2022/0043089 A1* 2/2022 Splitthoff ........... G01R 33/5608

OTHER PUBLICATIONS

Setsompop, Kawin, et al.: "Blipped-controlled aliasing in parallel imaging (blipped-CAIPI) for simultaneous multislice echo planar imaging with reduced g-factor penalty"; in: Magnetic Resonance in Medicine; vol. 67,5; pp. 1210-1224; 2012; DOI 10.1002/mrm. 23097; 2012.

Breuer, Felix A. et al.: "Controlled Aliasing in Parallel Imaging Results in Higher Acceleration (CAIPIRINHA) for Multi-Slice Imaging"; in: Magnetic Resonance in Medicine 53: S. 684-691 (2005); 2005.

* cited by examiner

METHOD FOR THE REDUCTION OF INTERFERENCE SIGNALS

CROSS-REFERENCE TO RELATED APPLICATIONS

The present application claims the benefit of the filing date of Germany patent application no. DE 10 2021 203 268.0, filed on Mar. 31, 2021, the contents of which are incorporated herein by reference in their entirety.

TECHNICAL FIELD

The disclosure relates to a method for the reduction of interference signals and, in particular, to doing so in magnetic resonance (MR) recordings of measured data, which has been recorded simultaneously from at least two slices from an examination object that comprises at least two different spin types.

BACKGROUND

Magnetic resonance (MR) technology is a known technology with which images of the inside of an examination object can be generated. Put simply, for this purpose the examination object is positioned in a magnetic resonance apparatus in a comparatively strong, static, homogeneous main magnetic field, also known as a B0 field, with field strengths from 0.2 tesla to 7 tesla and more, such that the nuclear spins thereof are orientated along the main magnetic field. Radio frequency excitation pulses (RF pulses) are irradiated into the examination object to trigger nuclear spin resonances that can be measured as signals, the nuclear spin resonances triggered are measured as what is known as k-space data and MR images are reconstructed on the basis thereof or spectroscopic data is recorded. For spatial encoding of the measured data, rapidly applied magnetic gradient fields, known as gradients for short, are superimposed on the main magnetic field. A schedule used that describes a chronological sequence of RF pulses and of gradients to be applied is described as a pulse sequence (schedule) or is also known as a sequence. The measured data is digitalized and stored as complex numerical values in a k-space matrix. From the k-space matrix that is filled with values, a relevant MR image can be reconstructed by means of a multi-dimensional Fourier transform, for example.

The method most widely used to generate echo signals after an excitation of nuclear spins is what is known as the spin echo method. In the simplest scenario, this involves the transverse magnetization being "flipped" so to speak by irradiating at least one RF refocusing pulse after irradiation of the RF excitation pulse, as a result of which the de-phased magnetization is rephased again and therefore, after a time known as the echo time TE, what is known as a spin echo SE is generated after the RF excitation pulse.

The excitation and measurement of the echo signals generated are repeated after a repetition time TR (for example by applying various gradients for spatial encoding) until the desired number of echo signals have been measured and stored in the k-space r to image the examination object.

Among SE sequences, it is the TSE ("Turbo Spin Echo") sequences in particular, which are also known by the names FSE ("Fast Spin Echo") or RARE ("Rapid Acquisition with Refocused Echoes"), that are widely used in clinical applications. The advantage of TSE sequences compared with a "simple" SE sequence is that after an RF excitation pulse, a plurality of refocusing pulses are applied, and that, as a result thereof, a plurality of spin echo signals SE are also generated after an excitation. As a result, the data recording is accelerated since fewer repetitions of the sequence with a different spatial encoding are required for all the desired data to be measured. Compared with conventional SE methods, the measurement time for the entire k-space is therefore reduced in TSE sequences according to the number of echo signals that are refocused and recorded after excitation, an effect known as the "turbo factor".

SUMMARY

The desire for faster and faster MR recordings in the clinical environment is currently leading to a renaissance in methods in which a plurality of images are recorded simultaneously. In general, these methods can be characterized by the fact that, at least for part of the measurement, transverse magnetization of at least two slices at the same time is used simultaneously for the imaging process ("multi-slice imaging", "slice-multiplexing"). In contrast with this method, in established "multi-slice imaging," the signal from at least two slices is recorded alternately, that is, completely independently of one another with a corresponding longer measurement time.

Known methods used for this are, for example, what is known as Hadamard encoding, methods with simultaneous echo-refocusing, methods with broadband data recording, or even methods that use parallel imaging in the slice direction. The latter methods also include for example the CAIPIRINHA technique, as described by Breuer et al. in "Controlled Aliasing in Parallel Imaging Results in Higher Acceleration (CAIPIRINHA) for Multi-Slice Imaging", Magnetic Resonance in Medicine 53, 2005, pp. 684-691, and the blipped CAIPIRINHA technique, as described by Setsompop et al. in "Blipped-Controlled Aliasing in Parallel Imaging for Simultaneous Multislice Echo Planar Imaging With Reduced g-Factor Penalty", Magnetic Resonance in Medicine 67, 2012, pp. 1210-1224.

Such slice-multiplexing methods use what is known as a multiband RF pulse to excite two or more slices at the same time or to otherwise manipulate them, for example to refocus or saturate them. Here, such a multiband RF pulse is for example a multiplex of individual RF pulses, which would be used for manipulating the individual slices that are to be manipulated at the same time. In order to be able to separate the resulting signals from the various slices, prior to multiplexing a different phase is imprinted in each case on the individual RF pulses, for example by adding a linear phase increase for instance, by means of which the slices in the local space are shifted with respect to one another. By multiplexing, one obtains, for example, a baseband-modulated multiband RF pulse from an addition of the pulse shapes of the individual RF pulses.

As described in the aforementioned article by Setsompop et al. for example, g-factor disadvantages due to shifts between the slices can be reduced by using gradient blips for instance, or the phases of the individual RF pulses can be modulated accordingly. As was likewise mentioned in the cited article by Setsompop et al. but also already described in the cited article by Breuer et al., the signals from the slices excited at the same time or otherwise manipulated can be combined initially, as signals from only one slice in order to then be separated in the post-processing using a parallel reconstruction method, for example a (slice) GRAPPA method (GRAPPA="Generalized Autocalibrating Partial Parallel Acquisition") or a different parallel imaging method (PPA), such as a SENSE ("Sensitivity encoding") method, for example.

For such a separation of slices involving collapsed recording, individually recorded reference data is typically used for each of the slices, said data having been measured in a pre-scan, for example.

If a slice-multiplexing method with the aforementioned gradient blips, and a TSE sequence for example, is used, it is possible in recordings without any suppression of spin signals from at least one type of tissue, for example in non-fat-saturated recordings, for ghosting artifacts to be observed in the resulting images.

The disclosure addresses the problem of reducing interference signals and hence artifacts in slice-multiplexing methods.

The disclosure is based on the realization that ghosting artifacts can result from a varying effect that the gradient blips used can have on spins in different types of tissue. Due to the difference in the resonance frequencies of spins present in different tissues, known as a chemical shift, in water and fat tissue for example, the spins in the different types of tissue are not excited in one and the same slice, but in slices that have been shifted in respect of one another by a slice distance $\Delta z$, where the following applies:

$$\Delta z = c * B0 / A_{GS},$$

where c corresponds to the chemical shift of the spins bound in different tissue types that have been considered, B0 to the strength of the main magnetic field, and $A_{GS}$ to the strength (amplitude) of the slice selection gradient (GS) applied for the slice selection of the RF pulses used.

Hence, the gradient blips used in the slice direction also induce different phase shifts, also known as "FOV (field of view) shifts", for spins bound in different types of tissue. This phase shift results from $Y * \Delta z * m_0$, where $m_0$ corresponds to the zeroth gradient moment of the gradient blip used and Y to the gyromagnetic ratio. For example, in the aforementioned blipped CAIPIRINHA technique, the gradient moment $m_0$ changes from k-space line to k-space line along which measured data is recorded. The phase, typically for the water signal, is corrected based on the gradient moment $m_0$ used for the respective k-space lines for the spatial encoding, either by a corresponding adjustment of the NCO (numerically controlled oscillator) used in the recording or retrospectively.

Generally speaking, the gradient blips are selected such that they produce the desired phase shift for spins bound in water, as a result of which, however, they produce a different phase shift for spins that are bound in fat, for example. As a result, artifacts, in particular what are known as ghosting fat artifacts, can appear in the image data reconstructed from measured data recorded in this way.

The problem is solved by a method for the recording of measured data, which has been recorded simultaneously by means of a magnetic resonance apparatus from at least two slices from an examination object that comprises at least two different spin types as described herein with respect to the various embodiments and claims.

A method according to the disclosure for recording measured data that has been recorded simultaneously by means of a magnetic resonance facility from at least two slices from an examination object comprising at least two different spin types comprises the steps:

Selecting a desired simultaneous recording of measured data from at least two slices in which recording phases that generate field of view shifts have been imprinted, Selecting a compensation factor to compensate for interference signals caused by the different spin types, Determining a compensation phase for the phases to be imprinted in the desired recording as a function of the compensation factor, Carrying out the desired recording of measured data and/or reconstruction of image data from the measured data by applying the compensation phase that has been determined to the respective phases to be imprinted.

By selecting a compensation factor that considers different spin types present in the examination object, interference signals caused by the different spin types can be corrected in a desired manner by means of compensation phases. The image quality of image data obtained using compensation phases according to the disclosure is therefore increased.

A magnetic resonance apparatus according to the disclosure comprises a magnet unit, a gradient unit, a radio frequency unit, and a control apparatus embodied (i.e. configured or otherwise implemented) to execute a method according to the disclosure with a compensation phase determination unit.

A computer program according to the disclosure implements a method according to the disclosure on a control apparatus when it is executed on the control apparatus.

The computer program can also be provided here in the form of a computer program product, which can be loaded directly into a memory of a control apparatus, with program coding means to execute a method according to the disclosure when the computer program product is executed in the computation unit of the computation system.

An electronically readable data carrier according to the disclosure comprises electronically readable control information stored thereon, which information comprises at least one computer program according to the disclosure and is embodied such that, when the data carrier is used in a control apparatus of a magnetic resonance facility, the control information executes a method according to the disclosure.

The advantages and explanations set out with reference to the method also apply by analogy to the magnetic resonance facility, the computer program product, and the electronically readable data carrier.

BRIEF DESCRIPTION OF THE DRAWINGS/FIGURES

Figure 2:
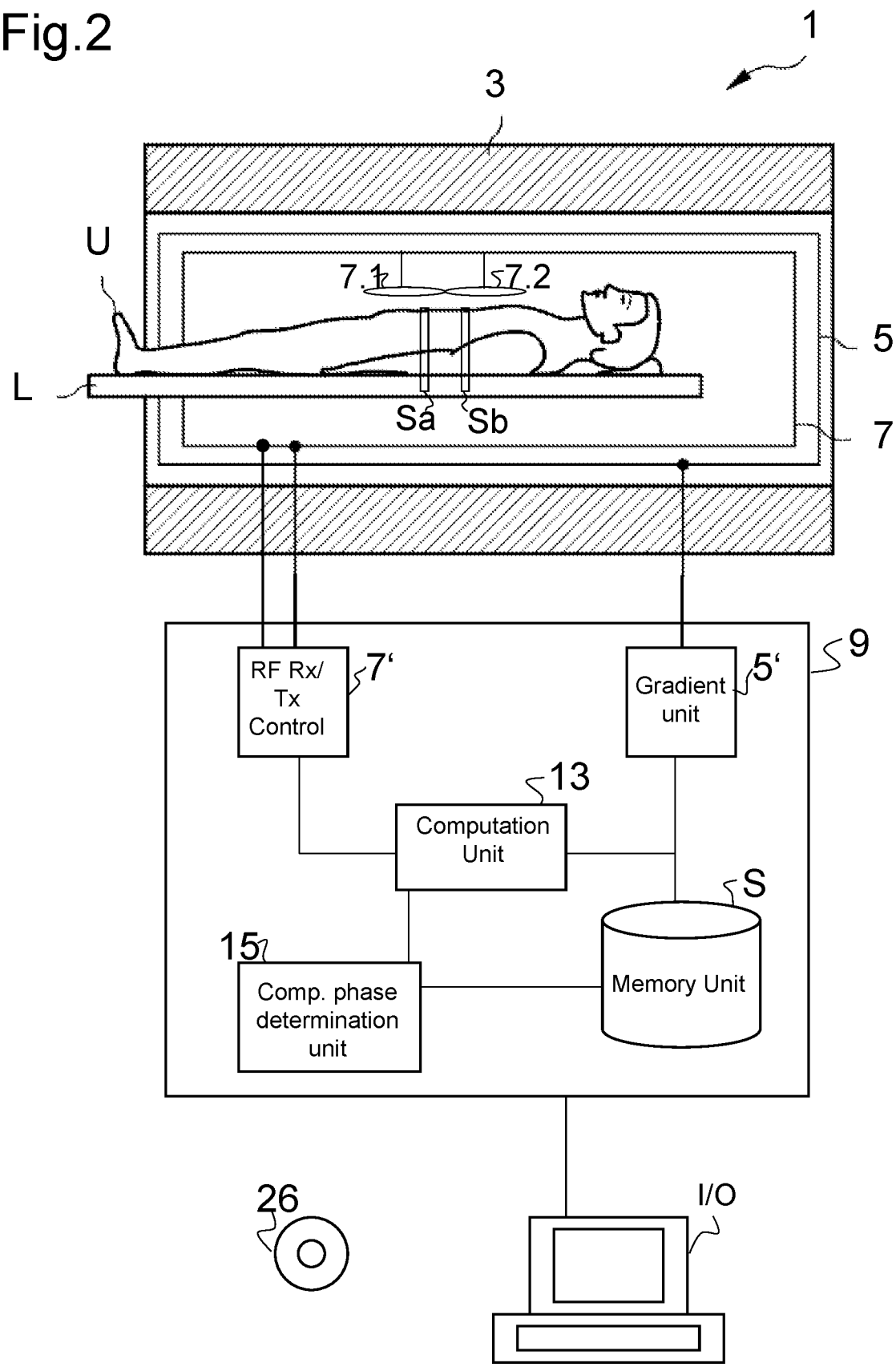

Further advantages and details of the present disclosure will emerge from the exemplary embodiments that are described hereinafter and from the drawing. The examples set out do not represent any restriction of the disclosure. The drawings show:

FIG. 1 illustrates an example schematic flow diagram of a method according to one or more embodiments of the disclosure, FIG. 2 illustrates an example schematic representation of the magnetic resonance facility according to according to one or more embodiments the disclosure.

DETAILED DESCRIPTION

FIG. 1 illustrates an example schematic flow diagram of a method according to one or more embodiments of the disclosure. The example flow diagram shown in FIG. 1 is for acquiring measured data MD that has been recorded simultaneously from at least two slices S1, . . . , Sn from an examination object comprising at least two different spin types, for example spins bound in water and in fat, by means of a magnetic resonance apparatus.

A desired recording of measured data that, simultaneously from at least two slices S1, ..., Sn (also referred to as a tuple of n slices), out of, for example, a total of N slices to be recorded N (N≥n) from the examination object, and in which, in particular in the slice direction, phases that generate field of view shifts have been imprinted during the recording, is selected (block 101). By selecting the desired recording, relevant phases P to be imprinted, which are generated by gradient blips, for example, are set.

As a desired recording, it is possible to select, for example, a simultaneous recording of n slices by means of a slice-multiplexing method, e.g. using gradient blips to imprint a phase shift, such as a blipped CAIPIRINHA method.

A compensation factor AF to compensate for interference signals caused by the different spin types is selected (block 103). The compensation factor AF indicates e.g. which of the at least two spin types is to be compensated for and how strongly.

For example, the compensation factor AF can be selected such that for two spin types it is between the values zero and one, where zero corresponds to a compensation for interference signals of the one spin type only and one corresponds to a compensation for interference signals of the other spin type only (AF=[0;1]). In other words, the values zero and one correspond to an optimization of the compensation for interference signals of precisely one of the two spin types in each case.

Advantageously, the compensation factor AF is selected such that not only interference signals of one spin type are compensated for, but that interference signals from at least two spin types occurring in the examination object are compensated for. In the aforementioned example, the value of the compensation factor AF is therefore between zero and one (AF=]0;1[). Such a compensation factor AF=]0;1[ does not mean an optimum compensation for any spin type, but interference signals are reduced overall.

The compensation factor AF can be selected as a function of a k-space position of the measured data MD to be recorded, for example as a function of the position of k-space lines to be sampled (AF=AF(k)). In this way, the image-spatial or frequency-spatial distribution of interference signals can be influenced. For example, the compensation factor AF can be selected such that interference signals in the image space are moved into a region where they are not superimposed on the examination object imaged. Such a region can be, for example, an oversampled region, if oversampling is intended in the desired recording, in the phase-encoding direction, for example. For this purpose, the compensation factor AF can be selected as a linear function of the k-space position, for example: AF~k.

Further functions are conceivable for a compensation factor AF to influence interference signals in a desired manner.

The compensation factor AF can also be selected, for example, as a random function. As a result, interference signals in the reconstructed image space are blurred and lose their local signal strength.

Therefore, the selection of the compensation factor AF can ensue taking into consideration a desired distribution V of possible interference signals.

If the compensation factor AF is selected as a function with changing values, an occasional overcompensation of interference signals of one spin type is permissible, wherein as a mean value for all the compensation factors (AF) applied in the desired recording, interference signals of not only one spin type are compensated for and no interference signals are overcompensated for. In the aforementioned example of the range of values]0;1[ for the compensation factor AF, it therefore holds good that individual values of AF can also fall outside this range of values, but the mean value of the compensation factor AF falls within the aforementioned range of values.

The selection of the compensation factor AF can additionally or alternatively ensue taking into consideration at least one recording parameter AP set by the desired recording. In this way, circumstances set by the desired recording can be taken into consideration.

A recording parameter AP taken into consideration can be a suppression of a spin type, for example. Desired recordings can make provision for different forms of suppression of a spin type with a different degree of suppression. The greater the extent to which signals of one spin type are suppressed, the fewer interference signals of this spin type are to be expected. Therefore, the compensation factor AF can set a lower compensation of interference signals from suppressed spin types, with the compensation that is set being lower, the greater the extent to which the spin type is suppressed. Conceivable for desired recordings are for example a strong fat suppression by means of SPAIR (spectral adiabatic inversion recovery), a weaker fat suppression by means of saturations or no suppression, wherein for the compensation factor AF, for example, values between 0 and 0.5 can be selected (with 0 representing no compensation for fat interference signals), in particular 0 in the case of strong fat suppression, 0.3 for average fat suppression, and 0.5 for the absence of fat suppression.

An additional or alternative recording parameter AP taken into consideration can be a signal strength of the at least two spin types. The compensation factor AF can be selected, for example, such that interference signals from a spin type with a stronger signal strength can be compensated for more intensively than interference signals of a spin type with a lower signal strength. In most contrast weightings of possible desired recordings (for example, T1-, T2-, or PD-weighted) the signal from the spin type fat is stronger than the signal from the spin type water.

The selection of the compensation factor (AF) can ensue taking into consideration a quantity QS of the at least two spin types in the examination object. A quantity QS of spin types can be determined for example by means of a pre-scan, e.g. a Dixon pre-scan or a frequency justification pre-scan (block 100). For example, for the spin types water and fat, the compensation factor can be determined in the frequency spectrum based on the integral via a measured fat peak $I_f$ and on the integral via a measured water peak $I_w$.

Here the compensation factor AF can be determined for example using a sigmoid-type function S as:

$$AF = S\left(\frac{I_f - I_w}{I_f + I_w}\right),$$

where the function S returns the value one (interference signals from water are compensated for) when the value in brackets is close to one and returns the value zero (interference signals from fat are compensated for) when the value in brackets is close to minus one.

The compensation factor AF for individual tuples of n slices that are to be measured in the desired recording, and from which tuples measured data is simultaneously recorded, can be selected independently in each case. Here a respective quantity of spin types and/or an image content expected according to the desired recording in the slices of a tuple or even a (diagnostic) relevance of the slices of a tuple can be taken into consideration. Slices on the edge of the entire batch of N slices to be recorded, in which the examination object is imaged to a lesser extent, can for example be regarded as less relevant than slices in the center of the batch of slices.

The compensation factor AF can be selected by a user. The user therefore has control over the compensation for the interference signals.

As a function of the compensation factor AF, a compensation phase dP is determined for phases P that are to be imprinted in the desired recording (block 105).

Compensation phases dP can be determined e.g. as a function of the corresponding phases that are to be imprinted, e.g. as a function of the zeroth moment of a gradient blip m0 that is applied to imprint the phases, or of a slice position of the respective spin types during the imprinting of the phases. If the gradient moment $m_0$ changes with the k-space line that has been read off, the compensation phase dP is therefore also dependent on the k-space position (on the k-space line).

A compensation phase can be determined as follows:

$$dP = Y*m_0*(z1-(c*AF*B0/A_{GS})),$$

with z1 being the excited slice position of a spin type considered, for example the slice position of water, c the chemical shift of two spin types considered, and $A_{GS}$ the amplitude of the slice selection gradient applied for the slice selection of the RF pulses used.

Here the term $c*AF*B0/A_{GS}$ denotes a spatial shift $\Delta z$ (regulated via the compensation factor) between a first spin type excited in the examination object and a second spin type excited in the examination object.

The determination of the compensation phase dP can therefore comprise a determination of a spatial shift $\Delta z = c*AF*B0/A_{GS}$ between a first spin type excited in the examination object and a second spin type excited in the examination object as a function of the compensation factor AF.

The desired recording of measured data MD and/or a reconstruction of image data BD from the measured data MD is performed by applying the compensation phase dP that has been determined to respective phases P that are to be imprinted (block 107).

Compensation phases dP that have been determined can be applied in the recording of the measured data MD, for example via a corresponding adjustment of the NCOs used.

Alternatively, compensation phases dP that have been determined can be applied in the reconstruction of the image data BD from the measured data MD, as a result of which a retrospective compensation of the phases ensues.

FIG. 2 shows in schematic form a magnetic resonance apparatus 1 according to the disclosure. This comprises a magnet unit 3 for generating the main magnetic field, a gradient unit (e.g. gradient generation circuitry) 5 for generating the gradient fields, a radio frequency unit (e.g. RF circuitry) 7 for irradiation and for receiving radio frequency signals, and a control apparatus (e.g. control circuitry) 9 embodied for carrying out a method according to the disclosure.

FIG. 2 shows these sub-units of the magnetic resonance facility 1 in a rough schematic form. For instance, the radio frequency unit 7 can consist of a plurality of sub-units, for example of a plurality of coils such as the coils 7.1 and 7.2, shown in schematic form, or more coils, which can either be embodied only to transmit radio frequency signals or only to receive the radio frequency signals that have been triggered, or can be embodied to do both.

For examining an examination object U, for example, a patient or also a phantom, said object can be inserted on a couch L into the magnetic resonance facility 1 into the measuring compartment thereof. Slices Sa and Sb exemplarily represent slices of the examination object that are to be recorded simultaneously, from which echo signals are to be recorded and acquired as measured data.

The control apparatus 9 is used to control the magnetic resonance facility 1 and e.g. may control the gradient unit 5 by means of a gradient control 5' and the radio frequency unit 7 by means of a radio frequency transmit/receive control (e.g. radio frequency transmit/receive control circuitry) 7'. Here, the radio frequency unit 7 can comprise a plurality of channels on which signals can be transmitted or received.

The radio frequency unit 7 is configured to, together with its radio frequency transmit/receive control 7', for facilitating the generating and irradiating (transmitting) a radio frequency alternating field to manipulate the spins in a region to be manipulated (for example, in slices S to be measured) in the examination object U. The center frequency of the radio frequency alternating field, also known as the B1 field, is generally set where possible such that it is close to the resonance frequency of the spins that are to be manipulated. Deviations of the center frequency from the resonance frequency are known as off-resonance. To generate the B1 field, controlled currents are applied on the RF coils in the radio frequency unit 7 by means of the radio frequency transmit/receive control 7'.

Furthermore, the control apparatus 9 comprises a compensation phase determination unit (e.g. compensation phase determination circuitry) 15, with which compensation factors can be selected and compensation phases can be determined. As a whole, the control apparatus 9 is embodied to execute any of the methods according to the disclosure.

A computation unit 13 comprised by the control apparatus 9 is embodied to carry out all the necessary computation operations for the necessary measurements and determinations. Interim results and results required for this purpose can be stored in a memory unit S of the control apparatus 9. The units shown are not necessarily to be understood as physically separate units, but merely represent a sub-division into units of meaning, which can also, however, be implemented for example in fewer or even in only one single physical unit.

Via an input/output device (I/O) of the magnetic resonance apparatus 1, control commands can be directed to the magnetic resonance facility by a user, for example, and/or results from the control apparatus 9 can be displayed as image data, for example.

A method described here can also be provided in the form of a computer program product, which comprises a program and implements the method described on a control apparatus 9 when it is carried out on the control apparatus 9. Likewise, an electronically readable data carrier 26 can be provided, with electronically readable control information stored thereon, which is embodied to comprise at least one such computer program product that has just been described and is embodied such that it carries out any of the methods as described herein when the data carrier 26 is used in a control apparatus 9 of a magnetic resonance facility 1.

The various components described herein may be referred to as "units." As noted above, such components may be implemented via any suitable combination of hardware and/or software components as applicable and/or known to achieve the intended respective functionality. This may include mechanical and/or electrical components, FPGAs, processors, processing circuitry, or other suitable hardware components configured to execute instructions or computer programs that are stored on a suitable computer readable medium. Regardless of the particular implementation, such units, as applicable and relevant, may alternatively be referred to herein as "circuitry," "processors," or "processing circuitry."

What is claimed is:

1. A method for acquiring measured data that has been recorded simultaneously, via a magnetic resonance apparatus, from at least two slices identified with an examination object comprising at least two different spin types, comprising:
selecting, via the magnetic resonance apparatus, a simultaneous recording of measured data from the at least two slices in which phases that generate field of view shifts are to be imprinted during the recording;
receiving, via the magnetic resonance apparatus, a compensation factor to compensate for interference signals caused by a chemical shift between the at least two different spin types;
computing, via the magnetic resonance apparatus, a compensation phase for the phases to be imprinted in the recording as a function of the compensation factor;
executing, via the magnetic resonance apparatus, the selected simultaneous recording of the measured data;
performing a reconstruction of image data from the measured data; and
displaying, via the magnetic resonance apparatus, the reconstructed image data,
wherein the computed compensation phase is applied to each respective one of the phases to be imprinted during the selected simultaneous recording of the measured data and/or during the reconstruction of image data from the measured data to reduce ghosting artifacts.

2. The method as claimed in claim 1, wherein the received compensation factor is based upon a predetermined distribution of possible interference signals.

3. The method as claimed in claim 1, wherein the received compensation factor is based upon a k-space position of the measured data that is to be recorded.

4. The method as claimed in claim 1, wherein the received compensation factor is based upon a quantity of the at least two spin types in the examination object.

5. The method as claimed in claim 1, wherein the received compensation factor is based upon at least one recording parameter set by the selected simultaneous recording.

6. The method as claimed in claim 5, wherein the at least one recording parameter is based upon a suppression of a spin type or a signal strength of the at least two spin types in the examination object.

7. The method as claimed in claim 1, wherein the received compensation factor is selected by a user.

8. The method as claimed in claim 1, wherein the received compensation factor is selected based upon a random function.

9. The method as claimed in claim 1, wherein the received compensation factor comprises a mean value of each one of a plurality of compensation factors applied in the selected simultaneous recording such that interference signals of more than one spin type are compensated.

10. The method as claimed in claim 1, wherein computing the compensation phase comprises computing a spatial shift ($\Delta z$) between a first spin type excited in the examination object and a second spin type excited in the examination object as a function of the received compensation factor.

11. A magnetic resonance apparatus for acquiring measured data that has been recorded simultaneously from at least two slices identified with an examination object comprising at least two different spin types, comprising:
a main magnet; and
control circuitry configured to cause the magnetic resonance apparatus to:
select a simultaneous recording of measured data from the at least two slices in which phases that generate field of view shifts are to be imprinted during the recording;
receive a compensation factor to compensate for interference signals caused by a chemical shift between the at least two different spin types;
compute a compensation phase for the phases to be imprinted in the recording as a function of the compensation factor;
execute the selected simultaneous recording of the measured data;
perform a reconstruction of image data from the measured data; and
display the reconstructed image data,
wherein the computed compensation phase is applied to each respective one of the phases to be imprinted during the selected simultaneous recording of the measured data and/or during the reconstruction of Mine data from the measured data to reduce ghosting artifacts.

12. A non-transitory computer-readable medium having instructions stored thereon that, when executed by one or more processors associated with a magnetic resonance apparatus, cause the magnetic resonance apparatus to acquire measured data that has been recorded simultaneously from at least two slices identified with an examination object comprising at least two different spin types by:
selecting a simultaneous recording of measured data from the at least two slices in which phases that generate field of view shifts are to be imprinted during the recording;
receiving a compensation factor to compensate for interference signals caused by a chemical shift between the at least two different spin types;
computing a compensation phase for the phases to be imprinted in the recording as a function of the compensation factor;
executing the selected simultaneous recording of the measured data;
perform a reconstruction of image data from the measured data; and
displaying the reconstructed image data,
wherein the computed compensation phase is applied to each respective one of the phases to be imprinted during the selected simultaneous recording of the measured data and/or during the reconstruction of image data from the measured data to reduce ghosting artifacts.

13. The method as claimed in claim 1, wherein the received compensation factor is indicative of an amount of compensation of the interference signals for each one of the at least two different spin types.

14. The method of claim 13, wherein the received compensation factor indicates a higher amount of compensation for a first interference signal of the at least two different spin types having a higher signal strength than a second interference signal of the at least two different spin types.

15. The method of claim 1, wherein the received compensation factor indicates which of the at least two different spin types is to be compensated and an amount of compensation.

16. The method of claim 15, wherein the received compensation factor comprises a value between 0 and 1.

17. The method of claim 1, wherein the compensation phase is computed as a function of a zeroth moment of a gradient blip that is applied to imprint each respective one of the phases.

18. The method of claim 1, wherein the compensation phase (dP) is computed for each of the at least two different spin types by evaluating:

$dP = Y * m_0 * (z1 - (c * AF * B0 / A_{GS}))$, wherein:

Y represents a gyromagnetic ratio, $m_0$ represents a zeroth gradient moment of a gradient blip that is applied to imprint a respective one of the phases, z1 represents an excited slice position of a respective one of the at least two different spin types, c represents a chemical shift of the respective one of the at least two different spin types, and AF represents the compensation factor, $A_{GS}$ represents an amplitude of a slice selection gradient applied for a slice selection of radio frequency (RF) pulses, and B0 represents a strength of the main magnetic field used for executing the selected simultaneous recording of the measured data.

19. The method as claimed in claim 1, wherein the received compensation factor comprises a linear function of k-space position.

* * * * *